US00PP33962P2

(12) United States Plant Patent
van Beuningen

(10) Patent No.: US PP33,962 P2
(45) Date of Patent: Feb. 22, 2022

(54) APPLE TREE NAMED 'PINOT PRINCE'

(50) Latin Name: ***Malus domestica* Borkh.**
Varietal Denomination: Pinot Prince

(71) Applicant: V.O.F. Gebr. van Beuningen, Kerk Avezaath (NL)

(72) Inventor: Hendrik Adriaan van Beuningen, Kerk Avezaath (NL)

(73) Assignee: V.O.F. Gebr. Van Benuingen, Kerk Avezaath (NL)

( * ) Notice: Subject to any disclaimer, the term of this patent is extended or adjusted under 35 U.S.C. 154(b) by 0 days.

(21) Appl. No.: 17/147,363

(22) Filed: Jan. 12, 2021

(51) Int. Cl.
*A01H 5/08* (2018.01)
*A01H 6/74* (2018.01)

(52) U.S. Cl.
USPC ..... Plt./161

(58) Field of Classification Search
USPC ..... Plt./156, 161
See application file for complete search history.

(56) References Cited

U.S. PATENT DOCUMENTS

PP18,482 P3 * 2/2008 Ligonniere ..... A01H 6/7418 Plt./161
PP18,483 P3 * 2/2008 Ligonniere ..... A01H 6/7418 Plt./161
PP21,722 P3 * 2/2011 Ligonniere ..... A01H 6/7418 Plt./161

* cited by examiner

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of Apple tree named 'Pinot Prince', characterized by its upright to outwardly spreading plant habit; moderately vigorous growth habit; numerous fruit produced per plant; fruits with bright red-colored skin; and tolerance to winter and spring frosts and suitable for Mediterranean climate conditions.

2 Drawing Sheets

Figure 1:
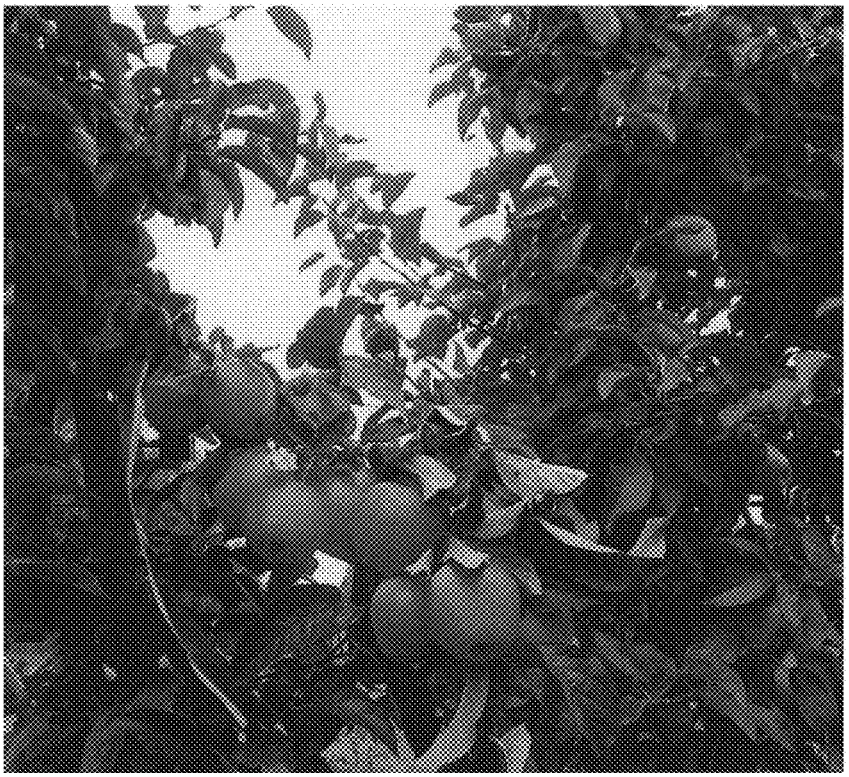

Botanical designation: *Malus domestica* Borkh.
Cultivar denomination: 'PINOT PRINCE'.

STATEMENT REGARDING PRIOR DISCLOSURES BY THE INVENTOR/APPLICANT & ASSIGNEE

An European Community Plant Breeder's Rights application for the instant plant was filed by the Applicant/Assignee, V.O.F. Gebr. van Beuningen of Kerk Avezaath, The Netherlands on Apr. 15, 2016, application number 2016/0938. Foreign priority is not claimed to this application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or the Applicant/Assignee. Inventor and Applicant/Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of Apple tree, botanically known as *Malus domestica* Borkh. and hereinafter referred to by the name 'Pinot Prince'.

The new Apple tree is a naturally-occurring branch mutation of *Malus domestica* Borkh. 'Pinova', disclosed in U.S. Plant Pat. No. 11,601. The new Apple tree was discovered and selected by the Inventor on a single tree of 'Pinova' grown in a controlled environment in Kerk Avezaath, The Netherlands in 2013.

Asexual reproduction of the new Apple tree by grafting in a controlled environment in Kerk Avezaath, The Netherlands since the spring of 2014 has shown that the unique features of this new Apple tree are stable and reproduced true to type in successive generations.

SUMMARY OF THE INVENTION

The new Apple tree has not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Pinot Prince'. These characteristics in combination distinguish 'Pinot Prince' as a new and distinct Apple tree:

1. Upright to outwardly spreading plant habit.
2. Moderately vigorous growth habit.
3. Numerous fruit produced per plant.
4. Fruits with bright red-colored skin.
5. Tolerant to winter and spring frosts and also suitable for Mediterranean climate conditions.

The new Apple tree differs primarily from trees of the female parent, 'Pinova', in fruit color as trees of the new Apple tree produce fruits without stripes on the skin whereas trees of 'Pinova' produce fruits with striped skin. In addition, fruit coloring of fruits of the new Apple tree starts four to six weeks earlier than fruits of 'Pinova'.

The new Apple tree can be compared to plants of *Malus domestica* Borkh. 'ROHO 3615', disclosed in U.S. Plant Pat. No. 17,672. In side-by-side comparisons, the new Apple tree differs primarily from trees of 'ROHO 3615' in fruit color as trees of the new Apple tree produce fruits without stripes on the skin whereas trees of 'ROHO 3615' produce fruits with striped skin.

BRIEF DESCRIPTION OF THE PHOTOGRAPHS

The accompanying photographs illustrate the overall appearance of the new Apple tree showing the colors as true as it is reasonably possible to obtain in colored reproductions of this type. Colors in the photographs may differ slightly from the color values cited in the detailed botanical description which accurately describe the colors of the new Apple tree.

The photograph on the first sheet (FIG. 1) comprises a side perspective view of typical trees of 'Pinot Prince' grown in an outdoor orchard.

Figure 2:
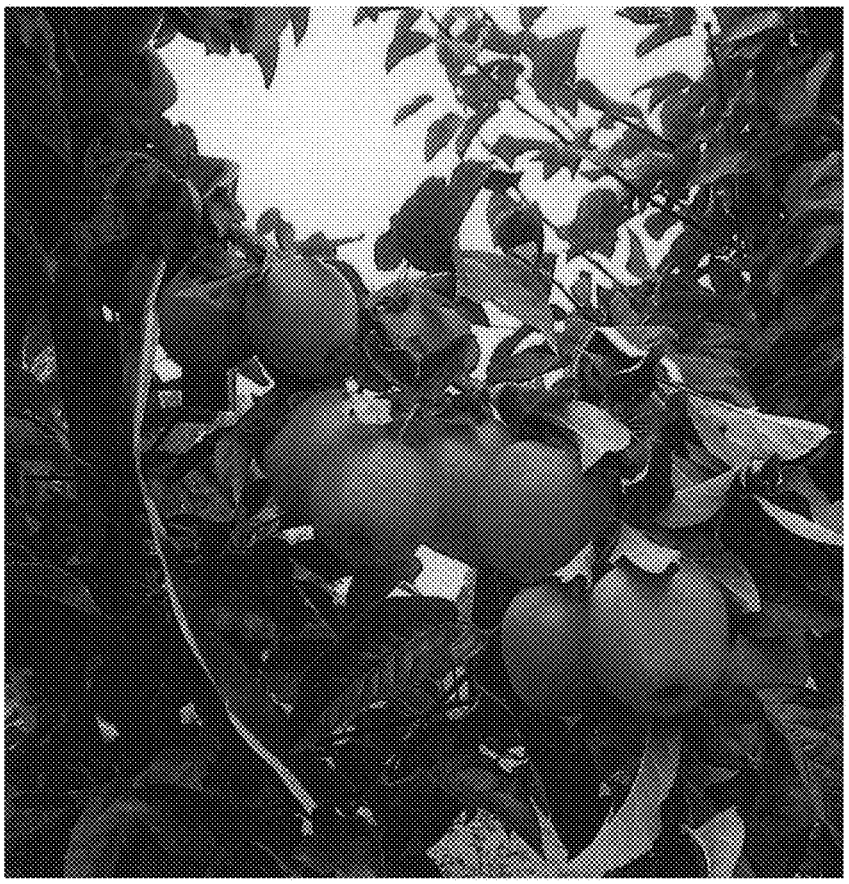

The photograph on the second sheet (FIG. 2) is a close-up view of a typical fruiting branch of 'Pinot Prince'.

DETAILED BOTANICAL DESCRIPTION

The aforementioned photographs, following observations and measurements describe trees grown during the late summer in Kerk Avezaath, The Netherlands in an outdoor orchard and under cultural practices typical of commercial Apple tree production. Trees were three years old when the photographs and description were taken. During the production of the trees, day temperatures ranged from 10° C. to 30° C. and night temperatures ranged from 8° C. to 15° C. Measurements and numerical values represent averages for typical trees and tree parts. The actual measurements of any individual tree or tree parts, or any group of trees or tree parts, of the new Apple tree may vary from the stated average. In the following description, color references are made to The Royal Horticultural Society Colour Chart, 2001 Edition, except where general terms of ordinary dictionary significance are used.

Botanical classification: *Malus domestica* Borkh. 'Pinot Prince'.

Parentage: Naturally-occurring branch mutation of *Malus domestica* Borkh. 'Pinova', disclosed in U.S. Plant Pat. No. 11,601.

Propagation:

*Type*.—Typically by grafting onto a rootstock.

Plant description:

*Plant and growth habit*.—Upright to outwardly spreading plant habit; moderately vigorous growth habit and moderate growth rate.

*Tree height*.—About three meters.

*Tree diameter*.—About 1 meter to 1.5 meter.

*Growth rate*.—About 20 cm to 30 cm per year.

*Lateral branch description*.—Length: About 40 cm to 70 cm. Diameter: About 3 cm to 5 cm. Internode length: About 3 cm to 10 cm. Strength: Strong, firm. Angle of attachment: About 60° to 75° from main trunk axis. Texture: Glabrous, woody. Color: Close to 166A to 166B.

*Leaf description*.—Arrangement: Alternate; simple. Length: About 7 cm to 10 cm. Width: About 4 cm to 6 cm. Shape: Ovate. Apex: Acute. Base: Obtuse to slightly cordate. Margin: Crenate to serrate. Texture, upper surface: Smooth, glabrous; undulate. Texture, lower surface: Rough, pubescent. Venation pattern: Pinnate. Color: Developing leaves, upper surface: Close to 144B. Developing leaves, lower surface: Close to 144C. Fully developed leaves, upper surface: Close to 143A; venation, close to 145A. Fully developed leaves, lower surface: Close to 143C; venation, close to 147D. Petioles: Length: About 3 cm to 5 cm. Diameter: About 2 mm to 4 mm. Texture, upper and lower surfaces: Smooth, glabrous. Color, upper and lower surfaces: Close to between 141C and 143A.

Flower description:

*Flower type and flowering habit*.—Single rotate flowers arranged on panicles; freely flowering habit with about six to ten flowers per inflorescence; flowers face mostly outwardly.

*Fragrance*.—Faintly fragrant, pleasant.

*Natural flowering season*.—Continuously flowering in April and May in The Netherlands.

*Flower longevity*.—Flowers last about 15 days on the plant; flowers not persistent.

*Inflorescence height*.—About 5 cm to 7 cm.

*Inflorescence diameter*.—About 7 cm to 10 cm.

*Flower diameter*.—About 2 cm to 3 cm.

*Flower depth* (*height*).—About 5 mm to 10 mm.

*Flower buds*.—Shape: Oval to rounded; distally, slightly tapering. Length: About 1 cm to 3 cm. Diameter: About 5 mm to 10 mm. Texture: Smooth, glabrous. Color: Close to 63A.

*Petals*.—Quantity and arrangement: Typically five in a single whorl; slightly imbricate. Length: About 1 cm to 1.5 cm. Width: About 5 mm to 10 mm. Shape: Obovate to elliptic. Apex: Obtuse. Base: Obtuse to acute. Margin: Entire. Texture, upper and lower surfaces: Smooth, glabrous; satiny. Color: When opening and fully opened, upper surface: Close to 155C slightly tinged with close to 56B. When opening and fully opened, lower surface: Close to 155C flushed with close to 57B.

*Sepals*.—Quantity and arrangement: Typically five in a single whorl. Length: About 5 mm to 7 mm. Width: About 3 mm to 5 mm. Shape: Ovate to somewhat deltoid. Apex: Acute. Base: Cordate. Margin: Entire. Texture, upper and lower surfaces: Rough, glabrous. Color, upper and lower surfaces: Close to 148B to 148C; distally, close to 63A.

*Pedicels*.—Length: About 3 cm to 5 cm. Diameter: About 2 mm to 4 mm. Strength: Moderately strong. Aspect: About 30° to 60° from stem. Texture: Smooth, glabrous. Color: Close to 143B.

*Reproductive organs*.—Stamens: Quantity: About 20 per flower. Filament length: About 2 cm. Filament color: Close to 149B. Anther length: About 4 mm to 6 mm. Anther shape: Bi-lobed. Anther color: Close to 11B. Pollen amount: Scarce. Pollen color: Close to 158A. Pistils: Quantity: About five per flower. Pistil length: About 1 cm. Stigma shape: Trumpet-shaped. Stigma color: Close to 154A. Style length: Less than 1 cm. Style color: Close to 150A. Ovary color: Close to 144A.

Fruit description:

*Ripening time*.—About 160 to 170 days.

*Yield*.—Higher than average; about 20 kg to 25 kg per container.

*Use*.—Fresh market.

*Length*.—About 7 cm to 8 cm.

*Diameter*.—About 7 cm to 8 cm.

*Fruit weight*.—Typically individual fruits will weigh between 160 to 190 gr depending on environmental conditions.

*General shape in profile*.—Conic.

*Depth of cavity*.—About 7 mm, flat.

*Width of cavity*.—About 2.5 cm.

*Depth of eye basin*.—Medium to deep; about 6 mm to 8 mm.

*Width of eye basin*.—Medium; about 2 cm to 2.5 cm.

*Fruit stalk length*.—Medium to long; about 2.5 cm to 3 cm.

*Fruit stalk diameter*.—About 2 mm.

*Fruit stalk color*.—Close to 176A.

*Fruit skin color*.—Ground color, more green than 1B, overlain with close to 44A; at harvest, almost all of the fruit skin is red in color; close to 44A.

*Lenticels*.—Quantity: Medium; more than 150 per fruit. Length: About 2 mm to 3 mm. Color: Close to 44A.

*Flesh texture*.—Firm, compact.

*Flesh color*.—Close to 10D.

*Flavor*.—Rich, aromatic.

*Locules*.—Quantity per fruit: Five. Length: About 2 cm. Width: About 1 cm. Shape: Ovate.

*Seeds*.—Quantity per locule: None to about three depending on environmental conditions. Length: About 5 mm to 7 mm. Diameter: About 3 mm to 5 mm. Shape: Obovate to elliptic. Color: Close to 200A.

Temperature tolerance: The new Apple tree has been observed to tolerate temperatures ranging from about −20° C. to about 35° C.

Pathogen & pest resistance: Trees of the new Apple have been observed to be slightly resistant to Apple Scab (*Venturia inaequalis*). Trees of the new Apple have not been observed to be resistant to pests and other pathogens common to Apple trees.

It is claimed:

1. A new and distinct Apple tree named 'Pinot Prince' as illustrated and described.

* * * * *